United States Patent [19]

Johnson et al.

[11] Patent Number: 5,556,847
[45] Date of Patent: Sep. 17, 1996

[54] METHODS OF EFFECTING MEMORY ENHANCEMENT MEDIATED BY STEROID SULFATASE INHIBITORS

[75] Inventors: David A. Johnson, Butler; Pui-Kai Li, Library; Michael E. Rhodes, Latrobe, all of Pa.

[73] Assignee: Duquesne University of the Holy Ghost, Pittsburgh, Pa.

[21] Appl. No.: 330,534

[22] Filed: Oct. 27, 1994

[51] Int. Cl.$^6$ .......................... A61K 31/56; A61K 31/57
[52] U.S. Cl. ........................................... 514/178; 514/182
[58] Field of Search ..................................... 514/178, 182

[56] References Cited

FOREIGN PATENT DOCUMENTS

92/01587 8/1992 WIPO .
92/07739 9/1992 WIPO .
92/08935 10/1992 WIPO .

OTHER PUBLICATIONS

Flood et al., "Dehydroepiandrosterone and its sulfate enhance memory retention in mice", *Brain Research*, vol. 447, pp. 269–278, 1988.
Flood et al., "Dehydroepiandrosterone sulfate improves memory in aging mice", *Brain Research*, vol. 448, pp. 178–181, 1988.
Flood et al., "Memory–enhancing effects in male mice of pregnenolone and steroids metabolically derived from it", *Proc, Nat'l. Acad. Sci. USA*, vol. 89, pp. 1567–1571, 1992.
Majewska, "Neurosteroids: Endogenous Bimodal Modulators of the GABA$_A$ Receptor. Mechanism of Action and Physiological Significance", *Progress in Neurobiology*, vol. 38, pp. 379–395, 1992.
Robel et al., "Neurosteroids: Biosynthesis and Function", *Trends Endocrinol Metab*, vol. 5, pp. 1–8, 1994.
Mellon, "SPECIAL ARTICLE— Neurosteroids: Biochemistry, Modes of Action, and Clinical Relevance", *Journal of Clinical Endocrinology and Metabolism*, vol. 78, No. 5, pp. 1003–1008, 1994.

*Primary Examiner*—Phyllis G. Spivack
*Attorney, Agent, or Firm*—Jolene W. Appleman; Eckert Seamans Cherin & Mellott

[57] ABSTRACT

This invention discloses a method for treating a patient for an illness selected from the group consisting of amnesia, head injuries, Alzheimer's disease, epileptic dementia, presenile dementia, post traumatic dementia, senile dementia, vascular dementia and post stroke dementia or individuals otherwise seeking memory enhancement. The method comprises providing a compound of formula (1)

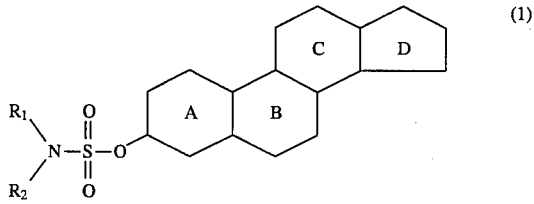

wherein (a) $R_1$ and $R_2$ are the same or different and are selected from the group consisting of hydrogen and a lower alkyl group of 1 to 6 carbon atoms and (b) the ring system ABCD is a steroid nucleus selected from the group consisting of estrone, dehydroepiandrosterone, estradiol, estradiolester, pregnenolone, substituted estrone, substituted dehydroepiandrosterone, substituted estradiol, substituted estradiolesters and substituted pregnenolone. The invention also discloses the enhancement of memory by the steroid sulfatase inhibitors of the invention acting synergistically with the naturally occurring neurosteroids dehydroepiandrosterone sulfate (DHEAS) and pregnenolone sulfate (PS).

45 Claims, 1 Drawing Sheet

METHODS OF EFFECTING MEMORY ENHANCEMENT MEDIATED BY STEROID SULFATASE INHIBITORS

BACKGROUND OF THE INVENTION

1. Field of the Invention

This invention relates to memory enhancement in patients suffering from illnesses consisting of amnesia, head injuries, Alzheimer's disease, epileptic dementia, presenile dementia, post traumatic dementia, senile dementia, vascular dementia and post-stroke dementia or individuals otherwise seeking memory enhancement. More particularly, the invention relates to the enhancement of memory by steroid sulfatase inhibitors and steroid sulfatase inhibitors in combination with the naturally occurring neurosteroids dehydroepiandrosterone sulfate (DHEAS) and pregnenolone sulfate (PS) and other structurally similar organic compounds.

2. Description of the Prior Art

Neurosteroids are concentrated within and are known to produce effects mediated by the central nervous system (CNS). Paul Robel and Etienne-Emile Baulile, *Neurosteroids, Biosynthesis and Function*, Trends Endocrinol Metab., Volume 5, pp. 1–8 (1994), disclose that several neurosteroids are involved in either auto-or paracrine mechanisms involving both regulation of target gene expression and effects on membrane receptors (including those of neurotransmitters).

Among the effects associated with neurosteroids is the enhancement of memory. James F. Flood, Gary E. Smith and Eugene Roberts, *Dehydroepiandrosterone and Its Sulfate Enhance Memory Retention in Mice*, Brain Research, Volume 447 pp. 269–278 (1988); James F. Flood, John E. Morley and Eugene Roberts, *Memory-Enhancing Effects in Male Mice of Pregnenolone and Steroids Metabolically Derived From It*, Proc. Nat'l Acad. Sci. USA, Volume 89, pp. 1567–1571 (1992) and James F. Flood and Eugene Roberts, *Dehydroepiandrosterone Sulfate Improves Memory in Aging Mice*, Brain Research, Volume 448, pp. 178–181 (1988).

The mechanism of this enhancement is not well understood but sulfated neurosteroids which enhance memory such as pregnenolone sulfate (PS) and dehydroepiandrosterone sulfate (DHEAS) are known to both inhibit the actions mediated by the $GABA_A$ receptor and facilitate NMDA receptors. The unsulfated analogs, pregnenolone and dehydroepiandrosterone, also enhance memory, however, they can also be metabolized to neurosteroids which have the opposite effect at the $GABA_A$ receptor. Synthia H. Mellon *Special Article Neurosteroids: Biochemistry, Modes of Action and Clinical Relevance*, Endocrinology and Metabolism, Volume 78, No. 5 pp. 1003–1008 (1994) and Majewska M.D.: *Neurosteroids: Endogenous Bimodal Modulators of the $GABA_A$ Receptor. Mechanism of Action and Physiological Significance*. Progress in Neurobiology, Volume 38, pp. 379–395 (1992).

PCT/US 92107739 published as WO93/04687 on Mar. 18, 1993 discloses methods for modulating NMDA-mediated ion transport and inhibiting non-NMDA glutamate-induced ion transport in neuronal cells. The methods involve contacting a neuronal cell with an effective mount of the neurosteroid pregnenolone sulfate and PCT/US92/08935 published as W093/07877 on Apr. 29, 1993 discloses memory enhancement by pregnenolone and pregnenolone sulfate. PCT/GB92/01587 published as WO/93/05064 on Mar. 18, 1993 disclosed that steroid sulfatase inhibitors are able to treat breast cancer.

Since the metabolism of pregnenolone and DHEA between the sulfated and unsulfated forms occurs bi-directionally within the central nervous system, it was previously unknown whether the sulfated or unsulfated forms produce memory enhancing effects individually or by way of metabolism from one analog to the other.

Therefore, in spite of the prior art disclosures, there remains a very real and substantial need for asteroid sulfatase inhibitor which can alter the equilibrium between the endogenous sulfated and unsulfated forms of DHEA in such a way to enhance memory. There is also a need to determine whether the memory enhancing effects of peripherally administered DHEAS and PS can be potentiated by inhibition of the metabolism of DHEAS and PS to DHEA and P, respectively, by way of preadministration of the steroid sulfatase inhibitors of the present invention.

SUMMARY OF THE INVENTION

The present invention has met the hereinbefore described need. The steroid sulfatase enzyme inhibitors of the present invention can inhibit greater than about 98% of the sulfatase after 24 hours. The present invention provides a process of using the steroid sulfatase inhibitors described herein for memory enhancement comprising providing a compound having the formula (1)

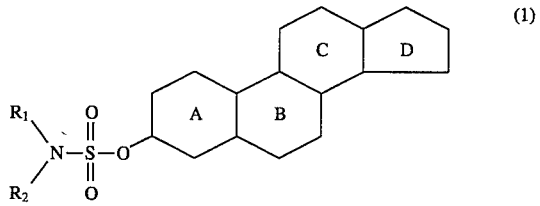

(1)

wherein (a) $R_1$ and $R_2$ may be the same or different and are selected from the group consisting of hydrogen and a lower alkyl group of one to six carbon atoms and (b) the ring system ABCD is asteroid nucleus selected from the group consisting of estrone, dehydroepiandrosterones, estradiol, estradiolesters, pregnenolone, substituted estrones, substituted dehydroepiandrosterones, substituted estradiol, substituted estradiolesters and substituted pregnenolone. The method comprises incorporating the compound in a suitable pharmaceutical carrier, administering a therapeutically or prophylactically effective amount of the compound incorporated in the carrier to a patient; and employing the method in treating a patient for memory enhancement.

Preferably $R_1$ is methyl and $R_2$ is hydrogen and most preferably both $R_1$ and $R_2$ are hydrogen. In the above structure (1), the steroid ring system is preferably estrone, dehydroepiandrosterone or pregnenolone. Other suitable steroid ring systems are:

Substituted estrones as follows:
  2-OH-estrone
  2-methoxy-estrone
  4-OH-estrone
  6 alpha-OH-estrone
  7 alpha-OH-estrone
  16 alpha-OH-estrone
  16 beta-OH-estrone Estradiols and substituted estradiols as follows:
  2-OH-17-beta estradiol
  2-methoxy-17 beta-estradiol
  4-OH-17-beta-estradiol 6 alpha-OH-17 beta-estradiol
7 alpha-OH-17 beta-estradiol
16 alpha-OH-17 beta-estradiol
16 beta-OH-17 alpha-estradiol
16 beta-OH-17 beta-estradiol
17 alpha-estradiol
17 beta-estradiol
17 alpha-ethinyl-17 beta-estradiol Estradiol esters and substituted estradiol esters, for example:
17-beta-OH-methyl estradiol ester
17-beta-OH-ethyl estradiol ester
17-beta-OH propyl-estradiol ester
17-beta-OH-butyl estradiol ester
17-beta-OH-penthyl-estradiol ester
17-beta-OH-hexyl-estradiol ester Substituted dehydroepiandrosterones, for example,:
6 alpha-OH-dehydroepiandrosterone
7 alpha-OH-dehydroepiandrosterone
16 alpha-OH-dehydroepiandrosterone
16 beta-OH-dehydroepiandrosterone Pregnenolone and substituted pregnenolone, for example:
6 alpha-OH-pregnenolone
7 alpha-OH-pregnenolone
16 alpha-OH-pregnenolone
16 beta-OH-pregnenolone This process provides a method of therapeutically treating a patient for an illness selected from the group consisting of amnesia, head injuries, Alzheimer's disease, epileptic dementia, presenile dementia, post traumatic dementia, senile dementia, vascular dementia and post stroke dementia. It also may treat other individuals that seek memory enhancement.

This invention provides a process for using the steroid sulfatase inhibitors described herein as synergistic agents with dehydroepiandrosterone sulfate (DHEAS) and/or pregnenolone sulfate (PS) to enhance the effect obtained treating a patient for one of either memory enhancement or therapeutically treating an illness selected from the group consisting of amnesia, head injuries, Alzheimer's disease, epileptic demential, presenile dementia, post traumatic dementia, senile dementia, vascular dementia and post stroke dementia.

It is an object of this invention to employ an effective dosage of the steroid sulfatase inhibitors for substantially enhancing the memory function.

It is an object of the present invention to employ steroid sulfatase inhibitors for use in treating a patient therapeutically.

It is an object of the present invention to employ steroid sulfatase inhibitors for use in prophylactically treating a patient.

It is a further object of this invention to employ an effective dosage of DHEAS with the steroid sulfatase inhibitors of this invention for a synergistic effect to further enhance the effect of treating a patient for one of either memory enhancement or therapeutically.

It is a further object of this invention to employ an effective dosage of PS with the steroid sulfatase inhibitors of this invention for a synergistic effect to further enhance the effect of treating a patient for one of either memory enhancement or therapeutically.

It is a further object of this invention to employ an effective dosage of DHEAS and PS with the steroid sulfatase inhibitors of this invention for a synergistic effect to further achieve memory enhancement.

It is yet a further object of this invention to use the steroid sulfatase inhibitors of this invention to increase the concentration of endogenous sulfated neurosteroids by way of inhibition of steroid sulfatase activity to enhance memory function and/or therapeutically.

It is yet another object of this invention to use the steroid sulfatase inhibitors of this invention to show that it is the sulfated form of DHEA and pregnenolone which is responsible for the memory enhancing properties of these neurosteroids.

It is another object of this invention to show that the steroid sulfatase inhibitors of the present invention alter the balance between sulfated and unsulfated neurosteroids.

It is yet another object of this invention to employ neurosteroids enhanced with the steroid sulfatase inhibitors of the present invention to reverse an illness such as amnesia induced by blockade of central muscarinic receptors.

It is a further object of this invention to employ blocking the metabolism of endogenous neurosteroids for enhancement of memory function which is similar to the blockade of monamine metabolism as a means of treating depression.

These and other objects of the invention will be more fully understood from the drawings and the following description of the invention and the claims appended hereto.

DESCRIPTION OF THE PREFERRED EMBODIMENTS

Figure 1:
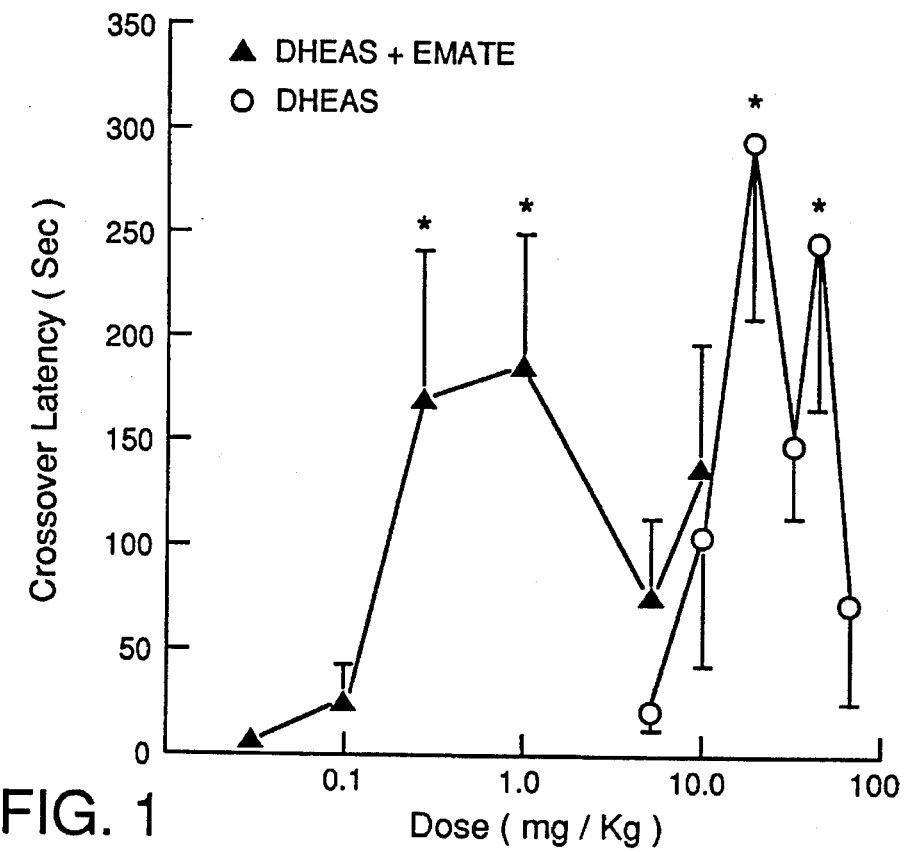
FIG. 1 shows the effect of DHEAS and the effect of DHEAS and sulfatase inhibitor EMATE on Scopolamine induced amnesia in rats.

As used herein, the term "patient" means members of the animal kingdom including, but not limited to, human beings.

The steroid sulfatase inhibitor compounds of this invention provide memory enhancing effects by altering the equilibrium between the endogenous sulfated and unsulfated form of the neurosteroids that occur naturally in the brain. These steroid sulfatase inhibitors and pharmaceutically acceptable salts inhibit the metabolism of the sulfated form of the neurosteroid to the unsulfated form and therefore inhibit the actions mediated by the $GABA_A$ receptor and facilitate NMDA receptors in the brain. They have a synergistic effect with DHEAS, PS and other neurosteroid memory enhancers. The compounds of this invention provide for the therapeutic treatment of an illness selected from the group consisting of amnesia, head injuries, Alzheimer's disease, epileptic dementia, presenile dementia, post traumatic dementia, senile dementia, vascular dementia and post stroke dementia. It may also treat other individuals that seek memory enhancement.

The method for treating a patient for memory enhancement comprising providing a compound having the formula (1)

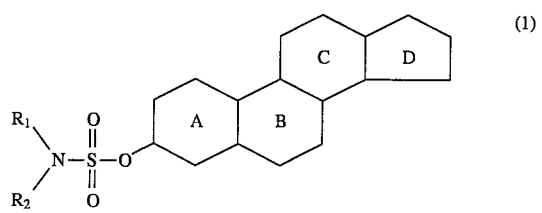

wherein (a) $R_1$ and $R_2$ may be the same or different and are selected from the group consisting of hydrogen (b) and a lower alkyl group of one to six carbon atoms. The ring system ABCD is asteroid nucleus selected from the group consisting of estrone, dehydroepiandrosterone, estradiol, estradiol ester, pregnenolone, substituted estrones, substituted dehydroepiandrosterones, substituted estradiols, substituted estradiol esters and substituted pregnenolone.

Preferably $R_1$ is methyl and $R_2$ is hydrogen and most preferably both $R_1$ and $R_2$ are hydrogen. In the above structure (1), the steroid ring system is preferably estrone, dehydroepiandrosterone or pregnenolone. Other suitable steroid ring systems are:

Substituted estrones as follows:
  2-OH-estrone
  2-methoxy-estrone
  4-OH-estrone
  6 alpha-OH-estrone
  7 alpha-OH-estrone
  16 alpha-OH-estrone
  16 beta-OH-estrone Estradiols and substituted estradiols, as follows:
  2-OH-17 beta-estradiol
  2-methoxy-17 beta-estradiol
  4-OH-17 beta-estradiol
  6 alpha-OH-17 beta-estradiol
  7 alpha-OH-17 beta-estradiol
  16 alpha-OH-17 beta-estradiol
  16 beta-OH-17 alpha-estradiol
  16 beta-OH-17 beta-estradiol
  17 alpha-estradiol
  17 beta-estradiol
  17 alpha-ethinyl-17 beta-estradiol Estradiol esters and substituted estradiol esters, for example:
  17-beta-OH-methyl-estradiol ester
  17-beta-OH-ethyl-estradiol ester
  17-beta-OH propyl-estradiol ester
  17-beta-OH-butyl-estradiol ester
  17-beta-OH-penthyl-estradiol ester
  17-beta-OH-hexyl-estradiol ester Substituted dehydroepiandrosterones, for example:
  6 alpha-OH-dehydroepiandrosterone
  7 alpha-OH-dehydroepiandrosterone
  16 alpha-OH-dehydroepiandrosterone
  16 beta-OH-dehydroepiandrosterone Pregnenolone and substituted pregnenolone, for example:
  6 alpha-OH-pregnenolone
  7 alpha-OH-pregnenolone
  16 alpha-OH-pregnenolone
  16 beta-OH-pregnenolone The method comprises incorporating the compound in a suitable pharmaceutical carrier, administering a therapeutically or prophylactically effective dosage of the compound incorporated in the carrier to a patient and employing the method in treating a patient for memory enhancement. The method also includes therapeutically treating a patient for an illness selected from the group consisting of amnesia, head injuries, Alzheimer's disease, epileptic dementia, presenile dementia, post traumatic dementia, senile dementia, vascular dementia and post stroke dementia. This method may also treat other individuals that seek memory enhancement.

The method also includes employing combining a therapeutically or prophylactically effective dosage of DHEAS and/or PS with the compounds of structure (1) to enhance the effect obtained treating a patient for one of either memory enhancement or an illness selected from the group consisting of amnesia, head injuries, Alzheimer's disease, epileptic dementia, presenile dementia, post traumatic dementia, senile dementia, vascular dementia and post stroke dementia.

One embodiment of the invention uses a method of treating a patient to enhance memory comprising providing a compound having the structure (2) wherein $R_1$ and $R_2$ may be the same or different and are selected from the group consisting of hydrogen and lower alkyl group of one to six carbon atoms.

A preferred embodiment using structure (2) is wherein $R_1$ is methyl and $R_2$ is hydrogen. A particularly preferred embodiment of the invention using structure (2) is wherein $R_1$ and $R_2$ are hydrogen.

Another embodiment of the invention uses a method of treating a patient to enhance memory by comprising providing a compound having the structure (3) wherein $R_1$ and $R_2$ can be the same or different and is selected from the group consisting of hydrogen and a lower alkyl group of one to six carbon atoms.

A preferred embodiment using structure (3) is wherein $R_1$ is methyl and $R_2$ is hydrogen. A particularly preferred embodiment using (3) is wherein $R_1$ and $R_2$ are hydrogen.

Another embodiment of the invention uses a method of treating a patient to enhance memory by comprising providing a compound having the structure (4) wherein $R_1$ and $R_2$ can be the same or different and selected from the group consisting of hydrogen and a lower alkyl group of one to six carbon atoms.

A preferred embodiment using structure 4 is wherein $R_1$ is methyl and $R_2$ is hydrogen. A particularly preferred embodiment of the invention using structure 4 is wherein $R_1$ and $R_2$ are hydrogen.

Another embodiment of this invention provides a method comprising providing a compound of this invention for therapeutic purposes. This process includes incorporating a compound of structure (2), (3) or (4) of this invention in a suitable pharmaceutical carrier and administering a therapeutically effective amount of the compound of this invention to a patient.

An example of a suitable pharmaceutical carrier is corn oil. The compounds of this invention incorporated into the pharmaceutical carrier may be administered to a patient by parenteral injection, such as for example, intravenously, intrathecally, intramuscularly or intraarterially. Other potential routes of administration include, for example, orally, transdermally or by other means. The dosage of, route of, administration of, and duration of therapy with the compounds of this invention, which can readily be determined by those skilled in the art, will be individualized according to the illness being treated, body weight of the patient, other therapy employed in conjunction with the compounds of this invention and the condition, clinical response and tolerance of the patient.

The following is an example of how a preferred compound is prepared and employed in the present invention:

EXAMPLE I

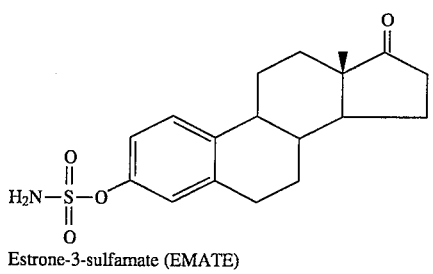

Estrone-3-sulfamate (EMATE)

The Synthesis of estrone - 3- sulfamate was as follows:

Sodium hydride (0.19 g, 2 eq) and sulfamoyl chloride (1.1 g, 2 eq) were added to a stirred solution of estrone (1.0 g) in anhydrous dimethyl formamide (25 ml) at 0° C. The solution was allowed to stir at room temperature for 24 hours. The reaction mixture was poured into a cold solution of sodium bicarbonate (50 ml) and the resulting aqueous phase was extracted with dichloromethane (3×40 ml). The combined dichloromethane was washed with distilled water (2×50 ml), dried ($MgSO_4$) and solvent evaporated in vacuo to afford 0.8 g of the crude product. The product was purified by silica gel chromatography eluted with dichloromethane—pet ether - ethyl acetate (1: 3: 0.5) mp 179°–181° C.; $^1H$ NMR (300 MHz; DMSO-d6) 0.83 (s, 3H, 18-$CH_3$), 6.98–73.6 (m, 3H, aromatic), 7.90 (s, 2H, $NH_2$). Analysis calculated for $C_{18}H_{23}NO_4S$: C, 61.87, H 6.63, N 4.01. Found C, 61.64, H 6.58, N 4.06.

The test methods were as follows:

Male rats weighing between 80 and 100 grams were purchased from Hilltop Lab Animals Inc. (Scottdale, Pa.) and housed in hanging wire mesh cages in groups of three with water and rat chow available ad libitum. The room in which the animals were housed was controlled for both temperature and humidity, there was a standard 12 hour, light/dark cycle. To assess memory, the Gemini Avoidance System (San Diego Instruments) was utilized in a standard passive avoidance paradigm. Briefly, the avoidance apparatus consisted of a box (53×53×32 cm) with two compartments connected by an opening with a sliding door. The room in which the rat was placed was brightly lit, while the other room was dark. Initially, the animals were allowed to explore the apparatus and were then removed. During the memory acquisition trial, animals were placed in the light compartment. When an animal entered the dark compartment, the sliding door closed and a mild foot shock (1mA; 1 sec.) was delivered. The rat was then removed from the apparatus and returned to its cage. Twenty-four hours later the rat was again placed in the light side of the apparatus and the time latency to crossing to the dark room recorded. If the rat did not enter the dark room within 10 minutes it was removed from the apparatus. The acquisition of memory for the foot shock was assessed as an increased latency period before entering the dark room on the second day. Significant differences in crossover latency were determined by statistical analysis utilizing one-way analysis of a variance with a Dunnett's test post hoc. Significant differences between groups were interpreted as differences in memory acquisition resulting from the various treatments.

To determine the effect of DHEAS on memory, one hour before the acquisition trial six groups of ten animals were injected intraperitoneally (IP) with one of the following several doses of DHEAS (5, 10, 20, 30, 50, 70 mg/Kg/ml dissolved saline) or saline. All animals in a given group were administered the same dosage. Thirty minutes prior to testing the animals were also injected IP with scopolamine (1 mg/Kg) which preliminary studies determined would produce amnesia in this paradigm. Twenty-four hours later the rats were again placed in the apparatus and the time delay before the animals entered the dark compartment was recorded.

To determine whether EMATE could potentiate the reversal of scopolamine-induced amnesia by DHEAS, additional groups of ten rats per group were administered EMATE (10 mg/Kg) suspended in corn oil IP 48 hours before the acquisition trial. On the day of the acquisition the six groups of trial animals were administered DHEAS and scopolamine as above, except that the dose range of DHEAS was reduced (0.03, 0.1, 0.3, 1.0, 5.0, 10.0 mg/Kg). Twenty-four hours later, crossover latency (the time delay before the rats crossed to the dark compartment) for the groups was determined.

In order to determine whether EMATE alone could enhance memory, four groups of rats (10 animals per group), were injected with EMATE (10 mg/Kg; IP), either four hours before the acquisition trial, or daily for 3, 10 or 15 days before the acquisition trial. Twenty-four hours following the acquisition trial crossover latency was determined. The dally dosage of EMATE was 10 mg/kg which inhibited the sulfatase enzyme for about three to four days. The reversal of the amnestic effect of scopolamine was tested 24 hours later.

The results were as follows:

In a preliminary study, control animals administered saline one hour before the acquisition trial with no scopolamine, had a prolonged retention latency the second day (583.8±16.2 sec), indicating a memory of the foot shock from the previous day. Rats administered saline one hour before the amnestic agent scopolamine (1 mg/Kg; IP) 30 minutes before the acquisition trial had a retention latency 24 hours later of only 21.1±10.9 sec indicating a failure to remember the aversive event of the previous day.

In the groups of animals administered DHEAS (IP) in various doses (5 –70 mg/Kg as administered before) one hour before the acquisition trial and scopolamine 30 minutes before, there was a significant ($p \leq 0.05$), reversal of scopolamine-induced amnesia which followed a bell shaped dose response curve (FIG. 1). The maximum effect occurred at 20 mg/Kg DHEAS with a crossover latency of 299.4±83.5 sec. For those groups of animals treated with both EMATE and DHEAS, there was a 20-fold increase in the potency of DHEAS with a maximum crossover latency of (194.9±54.6 sec at 1 mg/Kg). This result is shown in FIG. 1.

Figure 2:
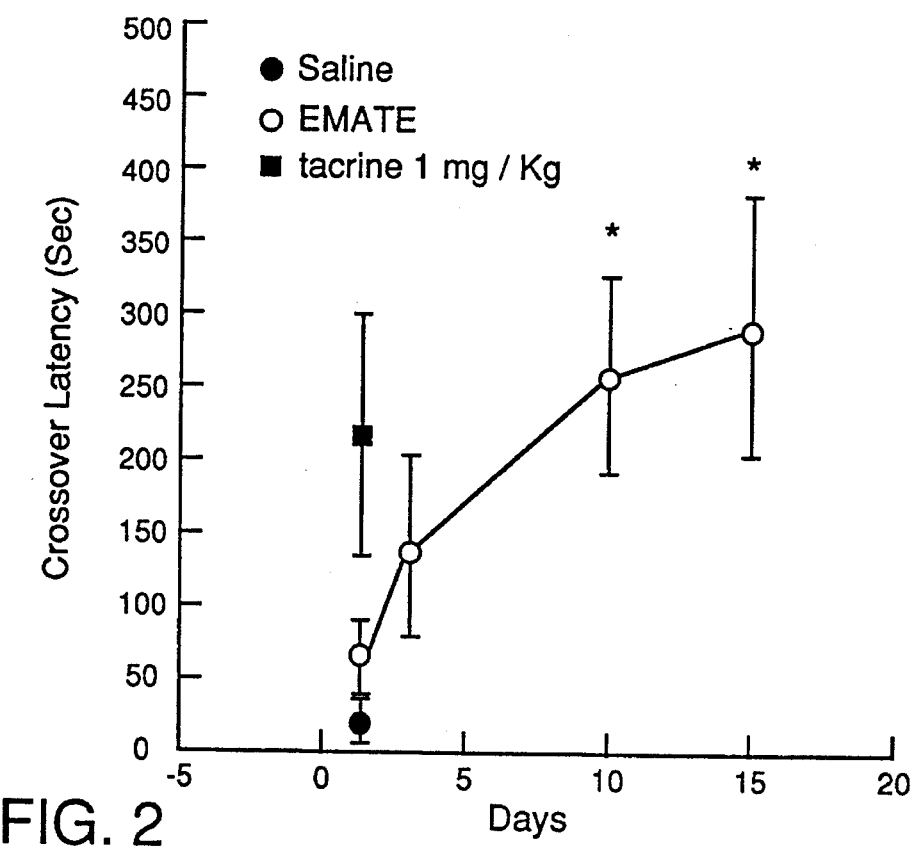
FIG. 2 discloses the effects of the sulfatase inhibitor EMATE alone on scopolamine induced amnesia in rats.

In those groups treated with EMATE alone, as a single dose EMATE failed to increase crossover latency (FIG. 2). However, in the groups administered EMATE daily for 10 and 15 days before the acquisition trial there was a significant ($p \leq 0.05$) reversal of scopolamine-induced amnesia with a crossover latency of 263.1 ±69.7 sec for the 10-day group and 297.0±88.7 sec for the 15-day group. Tacrine hydrochloride [COGNEX] is currently the only drug commercially available to treat Alzheimer's Disease associated dementia. Therefore, its effect on the reversal of scopolamine induced amnesia was included in the figure for comparison with our invention. This is shown in FIG. 2.

Sulfatase inhibitor EMATE can effect the memory enhancement of peripherally administered DHEAS, a neurosteroid, by inhibiting the metabolism of DHEAS to DHEA. EMATE is a potent irreversible inhibitor of steroid sulfatase. A single dose (10 mg/kg) can inhibit greater than 98% of sulfatase after 24 hours. After 10 days of treatment the sulfatase activity in the whole body (including liver, adrenal gland, ovary, uterus and brain) is inhibited. The administration of EMATE alone can alter the equilibrium between the endogenous sulfated and unsulfated forms of neurosteroids in such a way as to enhance memory.

The following sets forth a protocol that could be used in testing DHEA - Sulfamate:

EXAMPLE II

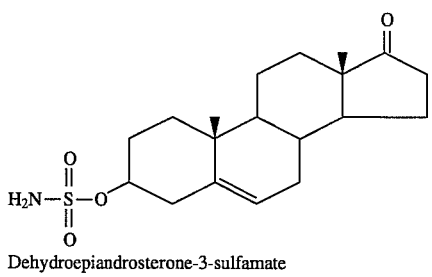

Dehydroepiandrosterone-3-sulfamate

The synthesis of dehydroepiandrosterone - 3- sulfamate [DHEA sulfamate] was as follows:

Sodium hydride (0.19 g, 2 eq) and sulfamoyl chloride (1.1 g, 2 eq) was added to a stirred solution of dehydroepiandrosterone (1.0 g) in anhydrous dimethyl formamide (25 ml) at 0° C. The solution was allowed to be stirred at room temperature for 24 hours. The reaction mixture was poured into a cold solution of sodium bicarbonate (50 ml) and the resulting aqueous phase was extracted with dichloromethane (3×40 ml). The combined dichloromethane was washed with distilled water (2×50 ml), dried ($MgSO_4$) and solvent evaporated in vacuo to afford the crude product. The product was purified by silica gel chromatography eluted with dichloromethane—pet ether—ethyl acetate (1: 3: 0.5).

To determine whether DHEA sulfamate would potentiate the reversal of scopolamine-induced amnesia by DHEAS, additional groups of ten rats per group as described above were administered DHEA sulfamate (10 mg/Kg) suspended in corn oil IP. On the day of the acquisition trial animals were administered DHEAS and scopolamine as above, except that the dose range of DHEAS was reduced (0.03, 0.1, 0.3, 1.0, 5.0, 10.0 mg/Kg). Each animal in a group gets the same dosage. On the following day crossover latency (the time delay before the rats crossed to the dark compartment) for the groups was determined.

In order to determine whether DHEA sulfamate alone could enhance memory, four groups of rats (10 animals per group), were injected with DHEA sulfamate (10 mg/Kg; IP), either four hours before the acquisition trial, or daily for 3, 10 or 15 days before the acquisition trial. Twenty-four hours following the acquisition trial crossover latency was determined.

The following sets forth a protocol that could be used in testing pregnenolone-3-sulfamate:

EXAMPLE III

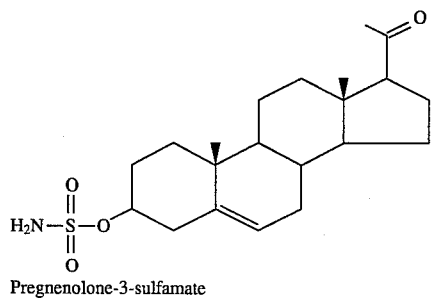

Pregnenolone-3-sulfamate

The synthesis of pregnenolone- 3 - sulfamate was as follows:

Sodium hydride (0.21 g, 2 eq) and sulfamoyl chloride (1.22 g, 2 eq) was added to a stirred solution of pregnenolone (1.0 g) in anhydrous dimethyl formamide (25 ml) at 0° C. The solution was allowed to stir at room temperature for 24 hours. The reaction mixture was poured into a cold solution of sodium bicarbonate (50 ml) and the resulting aqueous phase would be washed with distilled water (2×50 ml), dried ($MgSO_4$) and solvent evaporated in vacuo to afford the crude product. The product was purified by silica gel chromatograph eluted with dichloromethane—pet ether - ethyl acetate (1: 3: 0.5).

To determine whether pregnenolone sulfamate could potentiate the reversal of scopolamine-induced amnesia by DHEAS, additional groups of ten rats per group were administered pregnenolone sulfamate (10 mg/Kg) suspended in corn oil IP. On the day the acquisition groups of ten trial animals were administered DHEAS and scopolamine as above, except that the dose range of DHEAS was reduced (0.03, 0.1, 0.3, 1.0, 5.0, 10.0 mg/Kg). Each animal in a group get the same dosage. On the following day crossover latency (the time delay before the rats crossed to the dark compartment) for the groups was determined.

In order to determine whether pregnenolone sulfamate alone could enhance memory, four groups of rats (10 animals per group), were injected with pregnenolone sulfamate (10 mg/Kg; IP), either four hours before the acquisition trial, or daily for 3, 10, or 15 days before the acquisition trial. Twenty-four hours following the acquisition trial crossover latency was determined.

The experiments as discussed herein lead to the following conclusions:

EMATE and the other steroid sulfatase inhibitors of this invention can significantly enhance the potency of DHEAS in reversing scopolamine-induced amnesia. The significant enhancement of the potency of DHEAS by co-treatment with EMATE suggests that it is the sulfated form of DHEA which is responsible for the memory enhancing properties of this neurosteroid since the inhibition of steroid sulfatase enhanced rather than diminished the response to DHEAS.

The failure of EMATE alone to enhance crossover latency following a single dose indicated that the enzyme inhibitor by itself did not have the same mechanism of action for enhancing memory function as DHEAS. However, 10 days and 15 days of treatment with EMATE did have a significantly positive effect on memory acquisition. This positive effect may reflect an alteration in the balance between naturally occurring sulfated and unsulfated neurosteroids.

Although neurosteroids can alter hippocampal function, this is the first study to demonstrate the neurosteroids can reverse amnesia induced by blockade of central muscarinic receptors. The mechanism by which this occurs is not yet known precisely. It is thought that memory enhancement can be mediated by a strategy of blocking the metabolism of endogenous neurosteroids. DHEAS and PS enhance memory via inhibition of $GAGA_A$ receptor mediated actions and potentiation of NMDA receptor mediated actions. These effects are associated with memory enhancement. The inhibition of the metabolism of DHEAS and PS to DHEA and P respectively, results in higher concentrations of DHEAS and PS in the brain, therefore enhanced memory function. This strategy is similar to the use of monoamine oxidase inhibitors in the treatment of depression.

It will be understood by those skilled in the art that the compounds described herein may be used as synergistic agents with neurosteroids and other compounds.

It will be appreciated by those skilled in the art that the compounds of this invention may be used to transport other compounds, such as for example, DHEAS and PS, across the blood-brain barrier for distribution in the cerebrospinal fluid. It will be appreciated by those skilled in the art that both the transported compound and the compound of this invention will be active in the central nervous system after crossing the blood-brain barrier.

In order to effect the objects of this experiment this invention provides the use of the steroid sulfatase inhibitors of this invention for memory enhancement and a method of using these compounds in a patient for therapeutic and prophylactic purposes.

Whereas, particular embodiments of this invention have been described above for purposes of illustration, it will be evident to those skilled in the art that numerous variations of the details of the present invention may be made without departing from the invention as defended in the appended claims.

We claim:

1. A method for treating a patient to effect memory enhancement comprising providing a compound having the formula (1)

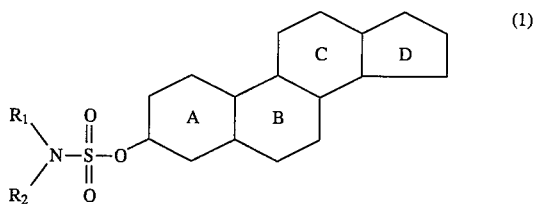

wherein (a) $R_1$ and $R_2$ may be the same or different and are selected from the group consisting of hydrogen and a lower alkyl group of 1 to 6 carbon atoms and (b) the ring system ABCD is a steroid nucleus selected from the group consisting of estrone, dehydroepiandrosterone, estradiol, estradiolester, pregnenolone, substituted estrones, substituted dehydroepiandrosterones, substituted estradiols, substituted estradiolesters and substituted pregnenolone, incorporating said compound in a suitable pharmaceutical carrier;

administering a dosage of said compound in said carrier which is therapeutically effective to enhance said memory of said patient.

2. The method of claim 1, comprising employing said method in therapeutically treating a patient having an illness selected from the group consisting of amnesia, head injuries, Alzheimer's disease, epileptic dementia, presenile dementia, post-traumatic dementia, senile dementia, vascular dementia and post stroke dementia in order to enhance said patient's memory.

3. The method of claim 1, comprising employing corn oil as said carrier.

4. The method of claim 2, comprising administering said compound incorporated in said carrier to a patient by the parenteral route.

5. The method of claim 2, comprising administering said compound in said carrier to a patient by the oral route.

6. The method of claim 2, comprising administering said compound incorporated in said carrier to enhance said patient's short term memory.

7. A method for treating a patient to effect memory enhancement comprising providing dehydroepiandrosterone sulfate (DHEAS) and a compound having the formula (1)

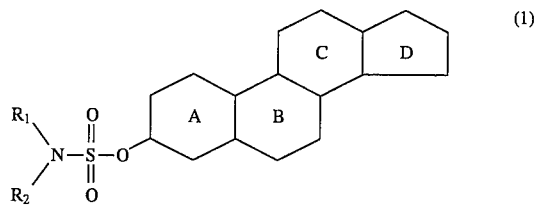

wherein (a) $R_1$ and $R_2$ may be the same or different and are selected from the group consisting of hydrogen and a lower alkyl group of one to six carbon atoms and (b) the ring system ABCD is asteroid nucleus selected from the group consisting of estrone, dehydroepiandrosterone, estradiol, estradiolester, substituted estrones, pregnenolone, substituted dehydroepiandrosterones, substituted estradiols, substituted estradiolesters and substituted pregnenolone, incorporating said compound in a suitable pharmaceutical carrier;

administering a dosage of said compound in said carrier which is therapeutically effective to enhance said memory of said patient.

8. The method of claim 7, comprising employing said method in therapeutically treating a patient having an illness selected from the group consisting of amnesia, head injuries, Alzheimer's disease, epileptic dementia, presenile dementia, post-traumatic dementia, senile dementia, vascular dementia and post stroke dementia in order to enhance said patient's memory.

9. A method for treating a patient to effect memory enhancement comprising providing pregnenolone sulfate (PS) and a compound of the formula (1)

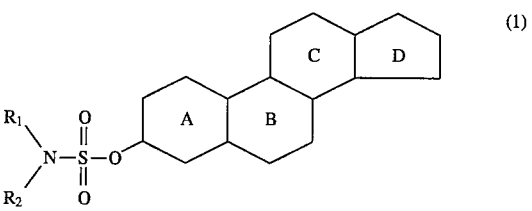

wherein (a) $R_1$ and $R_2$ may be the same or different and are selected from the group consisting of hydrogen and a lower alkyl group of one to six carbon atoms and (b) the ring system ABCD represents asteroid nucleus selected from the group consisting of estrone, dehydroepiandrosterone, estradiol, estradiolester, pregnenolone, substituted estrones, substituted dehydroepiandrosterones, substituted estradiols, substituted estradiolesters and substituted pregnenolone, incorporating said compound in a suitable pharmaceutical carrier;

administering a dosage of said compound in said carrier which is therapeutically effective to enhance said memory of said patient.

10. The method of claim 9, comprising employing said method in therapeutically treating a patient having an illness selected from the group consisting of amnesia, head injuries, Alzheimer's disease, epileptic dementia, presenile dementia, post-traumatic dementia, senile dementia, vascular dementia and post stroke dementia in order to enhance said patient's memory.

11. The method of claim 9, comprising employing an effective dosage of dehydroepiandrosterone sulfate (DHEAS) and pregnenolone sulfate (PS) with the compounds and pharmaceutically acceptable salts of formula (1),

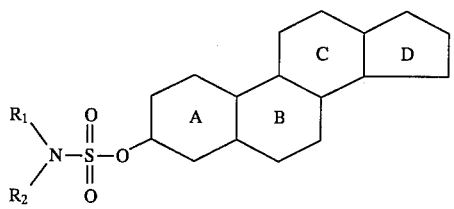

thereby enhancing the effect obtained treating a patient for one of either memory enhancement or an illness selected from the group consisting of amnesia, head injuries, Alzheimer's disease, epileptic dementia, presenile dementia, post-traumatic dementia, senile dementia, vascular dementia and post stroke dementia.

12. The method of claim 1 comprising employing an effective dosage of a compound having the species formula (2)

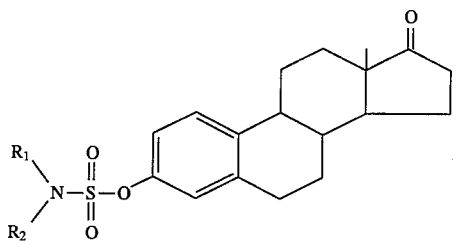

thereby enhancing the effect obtained treating a patient for one of either memory enhancement for an illness selected from the group consisting of amnesia, head injuries, Alzheimer's disease, epileptic dementia, presenile dementia, post traumatic dementia, senile dementia, vascular dementia and post stroke dementia.

13. The method of claim 12, comprising employing $R_1$ and $R_2$ equal to hydrogen in the compound.

14. The method of claim 12, comprising employing $R_1$ equal to methyl and $R_2$ equal to hydrogen in the compound.

15. The method of claim 12, comprising employing corn oil as said carrier.

16. The method of claim 12, comprising administering said compound incorporated in said carrier to a patient by the parenteral route.

17. The method of claim 12, comprising administering said compound in said carrier to a patient by the oral route.

18. A method for treating a patient to effect memory enhancement comprising providing dehydroepiandrosterone sulfate (DHEAS) and a compound having the species formula (2)

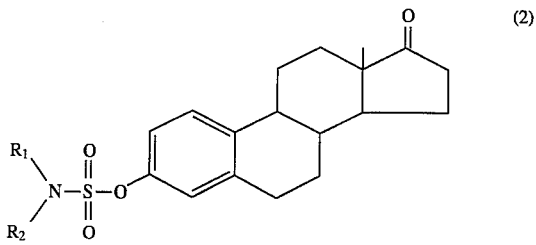

wherein (a) $R_1$ and $R_2$ may be the same or different and are selected from the group consisting of hydrogen and a lower alkyl group of one to six carbon atoms;

incorporating said compound in a suitable pharmaceutical carrier; and administering a dosage of said compound in said carrier which is therapeutically effective to enhance said memory of said patient.

19. The method of claim 18, comprising employing said method in therapeutically treating a patient having an illness selected from the group consisting of amnesia, head injuries, Alzheimer's disease, epileptic dementia, presenile dementia, post-traumatic dementia, senile dementia, vascular dementia and post stroke dementia in order to enhance said patient's memory.

20. A method for treating a patient to effect memory enhancement comprising providing pregnenolone sulfate (PS) and a compound having the species formula (2)

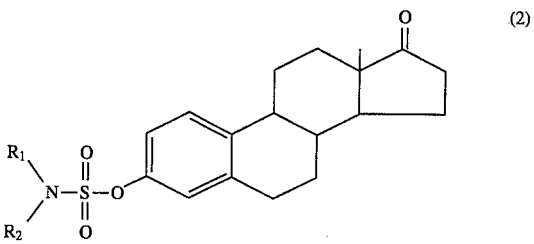

wherein (a) $R_1$ and $R_2$ may be the same or different and are selected from the group consisting of hydrogen and a lower alkyl group of 1 to 6 carbon atoms;

incorporating said compound in a suitable pharmaceutical carrier; and administering a dosage of said compound in said carrier which is therapeutically effective to enhance said memory of said patient.

21. The method of claim 20, comprising employing said method in therapeutically treating a patient having an illness selected from the group consisting of amnesia, head injuries, Alzheimer's disease, epileptic dementia, presenile dementia, post-traumatic dementia, senile dementia, vascular dementia and post stroke dementia in order to enhance said patient's memory.

22. The method of claim 20, comprising employing an effective dosage of dehydroepiandrosterone sulfate (DHEAS) and pregnenolone sulfate (PS) with the compound of the formula (2)

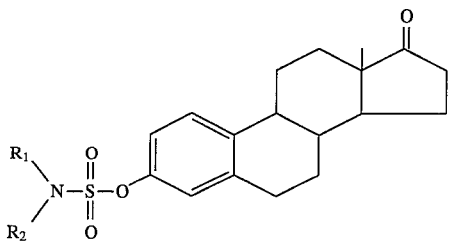

thereby enhancing the effect obtained treating a patient for one of either memory enhancement or an illness selected from the group consisting of amnesia, head injuries, Alzheimer's disease, epileptic dementia, presenile dementia, post-traumatic dementia, senile dementia, vascular dementia and post stroke dementia.

23. The method of claim 1 comprising employing an effective dosage of the compound having the species formula (3)

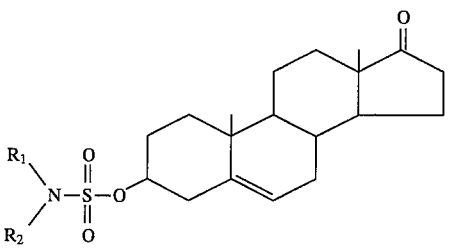

thereby enhancing the effect obtained treating a patient for one of either memory enhancement or an illness selected from the group consisting of amnesia, head injuries, Alzheimer's disease, epileptic dementia, presenile dementia, post traumatic dementia, senile dementia, vascular dementia and post stroke dementia.

24. The method of claim 23, comprising employing $R_1$ and $R_2$ equal to hydrogen in the compound.

25. The method of claim 23, comprising employing $R_1$ equal to methyl and $R_2$ equal to hydrogen in the compound.

26. The method of claim 23, comprising employing corn oil as said carrier.

27. The method of claim 23, comprising administering said compound incorporated in said carrier to a patient by the parenteral route.

28. The method of claim 23, comprising administering said compound in said carrier to a patient by the oral route.

29. A method for treating a patient to effect memory enhancement comprising providing dehydroepiandrosterone sulfate (DHEAS) and a compound of structure (3)

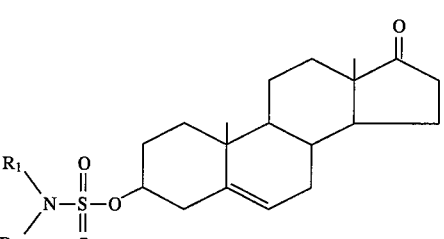

wherein (a) $R_1$ and $R_2$ may be the same or different and are selected from the group consisting of hydrogen and a lower alkyl group of one to six carbon atoms;

incorporating said compound in a suitable pharmaceutical carrier; and administering a dosage of said compound in said carrier which is therapeutically effective to enhance said memory of said patient.

30. The method of claim 29, comprising employing said method in therapeutically treating a patient having an illness selected from the group consisting of amnesia, head injuries, Alzheimer's disease, epileptic dementia, presenile dementia, post-traumatic dementia, senile dementia, vascular dementia and post stroke dementia in order to enhance said patient's memory.

31. A method for treating a patient to effect memory enhancement comprising providing pregnenolone sulfate (PS) and a compound having the species formula (3)

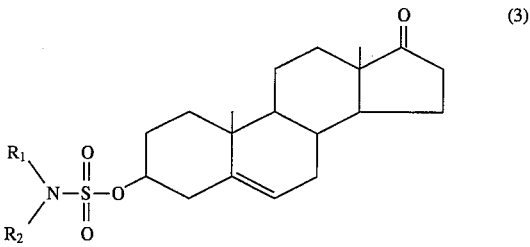

wherein (a) $R_1$ and $R_2$ may be the same or different and are selected from the group consisting of hydrogen and a lower alkyl group of 1 to 6 carbon atoms;

incorporating said compound in a suitable pharmaceutical carrier; and administering a dosage of said compound in said carrier which is therapeutically effective to enhance said memory of said patient.

32. The method of claim 31, comprising employing said method in therapeutically treating a patient having an illness selected from the group consisting of amnesia, head injuries, Alzheimer's disease, epileptic dementia, presenile dementia, post-traumatic dementia, senile dementia, vascular dementia and post stroke dementia in order to enhance said patient's memory.

33. The method of claim 31, comprising employing an effective dosage of dehydroepiandrosterone sulfate (DHEAS) and pregnenolone sulfate (PS) with the compound of the formula (3)

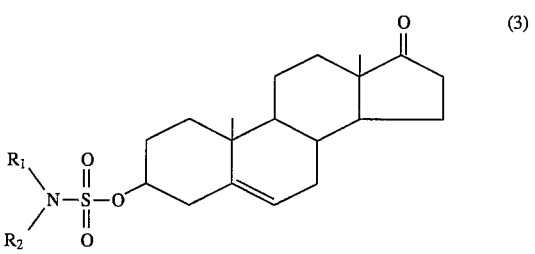

thereby enhancing the effect obtained treating a mammal for one of either memory enhancement or an illness selected from the group consisting of amnesia, head injuries, Alzheimer's disease, epileptic dementia, presenile dementia, post-traumatic dementia, senile dementia, vascular dementia and post stroke dementia.

34. The method of claim 1 comprising employing an effective dosage of a compound having the species formula (4)

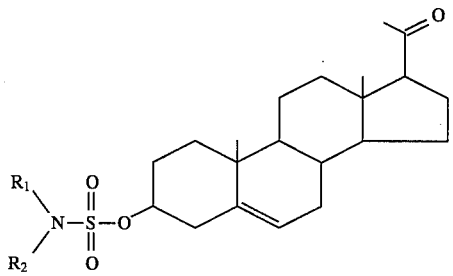

thereby enhancing the effect obtained treating a patient for one of either memory enhancement or an illness selected from the group consisting of amnesia, head injuries, Alzheimer's disease, epileptic dementia, presenile dementia, post-traumatic dementia, vascular dementia and post stroke dementia.

35. The method of claim 34, comprising employing said method in therapeutically treating a patient having an illness selected from the group consisting of amnesia, head injuries, Alzheimer's disease, epileptic dementia, presenile dementia, post-traumatic dementia, senile dementia, vascular dementia and post stroke dementia in order to enhance said patient's memory.

36. The method of claim 34, comprising employing $R_1$ and $R_2$ equal to hydrogen in the compound.

37. The method of claim 34, comprising employing $R_1$ equal to methyl and $R_2$ equal to hydrogen in the compound.

38. The method of claim 34, comprising employing corn oil as said carrier.

39. The method of claim 34, comprising administering said compound incorporated in said carrier to a patient by a parenteral route.

40. The method of claim 34, comprising administering said compound in said carrier to a patient by the oral route.

41. A method for treating a patient to effect memory enhancement comprising providing dehydroepiandrosterone sulfate (DHEAS) and a compound of structure species formula (4)

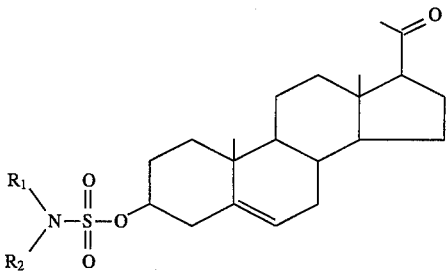

and wherein (a) $R_1$ and $R_2$ may be the same or different and are selected from the group consisting of hydrogen and a lower alkyl group of 1 to 6 carbon atoms;

incorporating said compound in a suitable pharmaceutical carrier; and administering a dosage of said compound in said carrier which is therapeutically effective to enhance said memory of said patient.

42. The method of claim 41, comprising employing said method in therapeutically treating a patient having an illness selected from the group consisting of amnesia, head injuries, Alzheimer's disease, epileptic dementia, presenile dementia, post-traumatic dementia, senile dementia, vascular dementia and post stroke dementia in order to enhance said patient's memory.

43. A method for treating a patient to effect memory enhancement comprising providing pregnenolone sulfate (PS) and a compound of species formula (4)

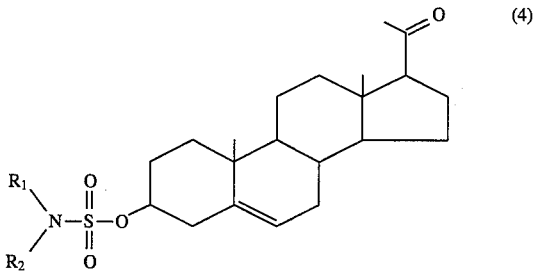

wherein (a) $R_1$ and $R_2$ may be the same or different and are selected from the group consisting of hydrogen and a lower alkyl group of 1 to 6 carbon atoms;

incorporating said compound in a suitable pharmaceutical carrier; and administering a dosage of said compound in said carrier which is therapeutically effective to enhance said memory of said patient.

44. The method of claim 43, comprising employing said method in therapeutically treating a patient having an illness selected from the group consisting of amnesia, head injuries, Alzheimer's disease, epileptic dementia, presenile dementia, post-traumatic dementia, senile dementia, vascular dementia and post stroke dementia in order to enhance said patient's memory.

45. The method of claim 44, comprising employing an effective dosage of dehydroepiandrosterone sulfate (DHEAS) and pregnenolone sulfate (PS) with the compound of the formula (4)

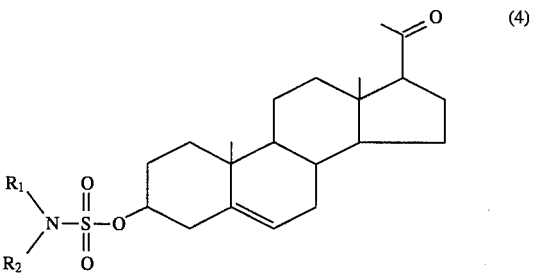

thereby enhancing the effect obtained treating a patient for one of either memory enhancement or an illness selected from the group consisting of amnesia, head injuries, Alzheimer's disease, epileptic dementia, presenile dementia, post-traumatic dementia, senile dementia, vascular dementia and post stroke dementia.

\* \* \* \* \*

UNITED STATES PATENT AND TRADEMARK OFFICE
CERTIFICATE OF CORRECTION

PATENT NO. : 5,556,847
DATED      : September 17, 1996
INVENTOR(S): DAVID A. JOHNSON, PUI-KAI LI and MICHAEL E. RHODES It is certified that error appears in the above-identified patent and that said Letters Patent is hereby corrected as shown below:

Column 1, line 63, "mount" should be --amount--.

Column 2, line 10, "asteroid" should be --a steroid--.

Column 2, line 41, "asteroid" should be --a steroid--.

Column 5, line 2, "asteroid" should be --a steroid--.

Column 8, line 3, after "dissolved" insert --in--.

Column 12, line 26, "asteroid" should be --a steroid--.

Column 12, line 57, "asteroid" should be --a steroid--.

Signed and Sealed this

Tenth Day of August, 1999

Attest:

Q. TODD DICKINSON

*Attesting Officer*    Acting Commissioner of Patents and Trademarks